(12) United States Patent
Bhagat et al.

(10) Patent No.: US 11,052,249 B2
(45) Date of Patent: Jul. 6, 2021

(54) NEUROMUSCULAR STIMULATION USING MULTISTAGE CURRENT DRIVER CIRCUIT

(71) Applicants: Nikunj Arunkumar Bhagat, New York, NY (US); Jose Luis Contreras-Vidal, Houston, TX (US)

(72) Inventors: Nikunj Arunkumar Bhagat, New York, NY (US); Jose Luis Contreras-Vidal, Houston, TX (US)

( * ) Notice: Subject to any disclaimer, the term of this patent is extended or adjusted under 35 U.S.C. 154(b) by 270 days.

(21) Appl. No.: 16/198,760

(22) Filed: Nov. 21, 2018

(65) Prior Publication Data

US 2020/0155841 A1    May 21, 2020

Related U.S. Application Data

(60) Provisional application No. 62/589,237, filed on Nov. 21, 2017.

(51) Int. Cl.
*H03K 3/26* (2006.01)
*A61N 1/36* (2006.01)
(Continued)

(52) U.S. Cl.
CPC ......... *A61N 1/36003* (2013.01); *A61N 1/025* (2013.01); *A61N 1/0452* (2013.01);
(Continued)

(58) Field of Classification Search
CPC ............. A61N 1/36003; A61N 1/0452; A61N 1/3603; A61N 1/0456; A61N 1/025;
(Continued)

(56) References Cited

U.S. PATENT DOCUMENTS 2,704,064 A * 3/1955 Fizzell ............... A61N 1/36
600/554
4,392,496 A 7/1983 Stanton
(Continued)

OTHER PUBLICATIONS

Milan Ilic, et. al., A programmable electronic stimulator for Fes systems, IEEE Transactions on Rehabilitation Engineering, 1994, 2(4), 234-239.
(Continued)

*Primary Examiner* — Michael C Zarroli

(57) ABSTRACT

Neuromuscular stimulation is widely used for rehabilitation and movement assist devices, due to its safety, efficacy, and ease of operation. For repeatable and accurate muscular contractions, a voltage controlled current sources (VCCS) with high compliance is required. Conventional VCCS design requires high-voltage rated operational amplifiers, which are expensive and consume large power. Moreover, conventional stimulators are not viable for simultaneous stimulation of muscle synergies, as they require multiple VCCS operating at the same time. This invention presents a neuromuscular stimulator with a multistage driver circuit wherein, a VCCS connected to an output driving stage comprising of folded-cascode transistor buffers and a bidirectional current mirror circuit. The multistage driver circuit uses inexpensive low-voltage rated operational amplifiers that consume 95% less power. Additionally, we disclose a stimulation method wherein only a single current source drives several output drivers connected in series or parallel to simultaneously stimulate multiple muscles or muscle synergies.

20 Claims, 7 Drawing Sheets

(51) Int. Cl.
   *A61N 1/04* (2006.01)
   *A61N 1/02* (2006.01)
(52) U.S. Cl.
   CPC ......... *A61N 1/0456* (2013.01); *A61N 1/3603* (2017.08); *H03K 3/26* (2013.01)
(58) Field of Classification Search
   CPC ........ A61N 1/36034; H03K 3/26; H03K 4/94; H03K 5/02; H03K 5/13
   USPC .......................................................... 607/48
   See application file for complete search history.

(56) References Cited

U.S. PATENT DOCUMENTS

| | | | |
|---|---|---|---|
| 5,514,165 A | 5/1996 | Malaugh | |
| 5,562,718 A | 10/1996 | Palermo | |
| 5,696,459 A * | 12/1997 | Neugebauer | H03F 3/005 323/315 |
| 5,775,331 A * | 7/1998 | Raymond | A61B 5/4893 600/554 |
| 5,954,758 A | 9/1999 | Peckham | |
| 6,762,646 B1 | 7/2004 | Bell | |
| 2004/0267333 A1* | 12/2004 | Kronberg | A61N 1/326 607/72 |
| 2007/0043398 A1* | 2/2007 | Ternes | A61N 1/36135 607/18 |
| 2008/0058783 A1* | 3/2008 | Altshuler | A61B 18/20 606/9 |
| 2016/0015977 A1* | 1/2016 | Biele | A61N 1/36125 607/46 |
| 2017/0281941 A1* | 10/2017 | Page | A61N 1/0456 |
| 2020/0289833 A1* | 9/2020 | Dellamano | A61N 1/0526 |

OTHER PUBLICATIONS

Wen-Whe Sue, et al., A high DC-gain folded-cascode CMOS operational amplifier, In Proceedings of IEEE Southeastcon '98 'Engineering for a New Era', 1998, 176-177, Orlando, USA.

Christopher Poletto, et. al., A high voltage, constant current stimulator for electrocutaneous stimulation through small electrodes, IEEE Transactions on Biomedical Engineering, 1999, 46(8), 929-936.

J. E. Ross, et al., Design of a PC controlled constant current stimulator for evoked potential studies, In Proceedings of the 22nd Annual International Conference of the IEEE Engineering in Medicine and Biology Society, 2000, vol. 4, 2594-2596, Chicago, USA.

J. A. De Lima, et al., A simple constant-current neural stimulator with accurate pulse-amplitude control, In Proceedings of the 23rd Annual International Conference of the IEEE Engineering in Medicine and Biology Society, 2001, vol. 2, 1328-1331, Istanbul, Turkey.

Han-Chang Wu, et al., A versatile multichannel direct-synthesized electrical stimulator for FES applications, IEEE Transactions on Instrumentation and Measurement, 2002, 51(1).

John Caldwell, A high-voltage bidirectional current source, Texas Instruments, 2013, Dallas, USA.

Chandrashekar Shendkar, et al., Design and development of a low-cost biphasic charge-balanced functional electric stimulator and its clinical validation, Healthcare Technology Letters, 2015, 2(5), 129-134.

Jesse Cornman, et al., A portable, arbitrary waveform, multichannel constant current electrotactile stimulator, International IEEE/EMBS Conference on Neural Engineering, 2017, 300-303, Shanghai, China.

David Karpul, et al., Low-power transcutaneous current stimulator for wearable applications, BioMedical Engineering Online, 2017, 16(1).

* cited by examiner

NEUROMUSCULAR STIMULATION USING MULTISTAGE CURRENT DRIVER CIRCUIT

CROSS-REFERENCE TO RELATED APPLICATIONS

This application claims the benefit of provisional patent application Ser. No. 62/589,237, filed 2017 Nov. 21 by the present inventors, which is incorporated by reference in its entirety.

REFERENCES CITED

U.S. Patents

| | | | |
|---|---|---|---|
| 5,562,718 | June 1994 | Palermo | 607/46 |
| 5,514,165 | May 1996 | Malaugh, et al | 607/46 |
| 6,762,646 B1 | July 2004 | Bell | 330/257 |

U.S. Patent Application Publications

| | | | |
|---|---|---|---|
| 20170281941A1 | October 2017 | Page et al | A61N 1/36021 |

Non-patent Literature Documents

1) Wen-Whe, et al., (1998) A high DC-gain folded-cascode CMOS operational amplifier. In Proceedings of IEEE Southeastcon '98 'Engineering for a New Era', Orlando, Fla., USA, 1998, pp. 176-177.
2) Wu, et al., (2002). A versatile multichannel direct-synthesized electrical stimulator for FES applications. IEEE Transactions on Instrumentation and Measurement, 51(1), 2-9.
3) Caldwell, (2013). A high-voltage bidirectional current source. Texas Instruments, technical note.
4) Shendkar, et al., (2015). Design and development of a low-cost biphasic charge-balanced functional electric stimulator and its clinical validation. *Healthcare Technology Letters*, 2(5), 129-134

BACKGROUND OF THE INVENTION

Neuromuscular electrical stimulation (NMES) is the application of short electrical pulses to externally depolarize nerves and muscle fibers, in order to evoke action potentials as well as to contract the muscle tissue. NMES has been used in rehabilitation for restoring functional movements such as grasping, walking, etc. to paralyzed patients, as well as to prevent muscle atrophy after a stroke or spinal cord injury. NMES can be applied on the desired nerve or muscle using either transcutaneous (i.e. through the skin), percutaneous or implanted electrodes. Typically, charge-balanced biphasic current pulses, comprising of a negative phase followed by a positive phase with sufficient interphase delay are used, to minimize tissue damage and electrode corrosion. The shape of the biphasic pulses can be symmetrical or asymmetrical. To maintain charge-balance for both types of pulses, the area (i.e., charge per phase) of the negative and positive phases are equal.

The design of a neuromuscular stimulator or NMES consists of a voltage controlled current source (VCCS) that is configured to provide constant current stimulation. The VCCS must be high voltage compliant to ensure that it can source or sink desired current through the tissue, despite presence of large tissue impedances. To implement this capability, the VCCS is powered by a high voltage source ranging from 100 to 300V. U.S. Pat. No. 5,562,718 disclosed a system and method for stimulating atrophied muscles of a patient using a micro-computer that was capable of generating sequential or overlapping pulse trains. Their design of the VCCS, comprised of a transformer isolated current transistor.

With the advancement in solid-state devices, recent NMES designs published in the literature have implemented the VCCS using current mirror circuits (Wu et al., 2002). Conventional transistor-based current mirror circuits are susceptible to parameter variations and it is challenging to regulate their output current. Instead, (Shendkar, et al., 2015) used a bidirectional VCCS known as the modified Howland current pump, which has more stable performance than conventional current mirror circuits. The Howland pump circuit comprises of an operational amplifier (op-amp), with precision resistors in its positive and negative feedback paths. Since the output voltage of an op-amp is cannot exceed its supply voltage, to achieve high voltage compliance with the conventional Howland pump, the supply voltage of the op-amp must be very high (e.g. 100-300V). This requires a special-purpose, high-voltage rated operational amplifier (op-amp, e. g. PA341 DF from Cirrus Logic can operate up to 350V) which are expensive and consume large power. To forego the expensive op-amp, a bootstrapped Howland pump was developed by (Caldwell, 2013) and was also used in U.S. Patent Application No. 20170281941A1. While, the bootstrapped implementation is cheaper, it is susceptible to common-mode latch-up issue and hence, requires an op-amp with extremely wide common-mode input voltage range.

SUMMARY

The prior art review, revealed two significant limitations in the present neuromuscular stimulation devices. Firstly, the voltage-controlled current source (VCCS) design using the conventional Howland pump requires very high-voltage rated op-amps, which are expensive and consume high quiescent power. Alternatively, the bootstrapped Howland pump implementation requires a wide input common-mode op-amp. Although, such op-amps are cheaply available, they have a limited output current capacity (e. g. for INA149 from Texas Instruments, maximum output current ≤±25 mA), which makes them suitable only in a few applications.

A second limitation is that in the conventional stimulation approach, one stimulation channel stimulates a single muscle at a time. A typical stimulator's channel has two conducting leads—a forward lead for driving current into the muscle and a return lead for completing the circuit. Some multi-channel stimulators, have used a common return lead for multiple forward leads. Still some other stimulators, have multiplexed the forward and return leads to selectively activate one muscle at a time. However, this approach is not economical for simultaneous stimulation of multiple muscles, as it will require multiple stimulation channels that operate at approximately the same time (U.S. Pat. No. 5,514,165). Simultaneous muscle stimulation is useful in activating muscle synergies, e.g. during walking, sit to stand, etc. as well as for bilateral activation of upper-limbs, e.g. when holding a glass in one hand and pouring water with other.

To overcome abovementioned limitations, this disclosure presents a neuromuscular electrical stimulator (NMES) with a multistage driver circuit wherein, the multistage driver circuit comprises of a VCCS connected to an output driving stage with sourcing and sinking current mirror circuits. The multistage driver circuit enabled the NMES to generate high-voltage compliant constant current pulses, using low-cost components that operate at 95% less quiescent power, for electrically stimulating nerves and muscles. Additionally, to simultaneously stimulate multiple muscles, we disclose a stimulation method wherein a single multistage driver supplies current to first muscle, and the return lead from first muscle is used to drive current through another muscle or several other muscles. Further, using a network of switches and resistors, we can selectively divert or attenuate the current in the subsequent output drivers and thus, proportionally control the current intensities of multiple simultaneously stimulated multiples.

In the present embodiment, the VCCS generates an output current proportional to the input voltage. The output current is then transferred to a bidirectional current mirror circuit via a pair of unity-gain buffers comprising of folded-cascode bipolar transistors. The impedance matching providing by the unity-gain buffers, allows the VCCS and current mirror circuits to operate using different supply voltages. This allowed us to implement the VCCS using the conventional Howland pump with inexpensive low-voltage rated op-amps. It also allowed the output driver circuit to provide very high-voltage compliance using inexpensive high-voltage rated transistors.

As compared to the bootstrapped Howland pump design discussed previously, the present VCCS does not limit the output current capacity, since it does not require wide common mode input capability or high-voltage rated op-amps. Any general-purpose, low-cost op-amp with desired current output capacity can be used. The Howland current pump based voltage controlled current source (VCCS) is suggested in the literature to have high tolerance to resistance mismatch, linear and accurate performance. However, a person skilled in the art will be able to implement the VCCS with any current pump or constant current source.

In the present embodiment, the modified Wilson's current mirror circuit is used to implement the output driving stage. However, any current mirror circuit topology can be used for the output stage, as well as any high-voltage rated transistor can be used to achieve desired voltage compliance. The multistage circuit allows the output current to be controlled using the high-precision VCCS, without having to deal with nonlinearities of conventional current mirror circuits.

The folded-cascode topology, although known in the literature, it has previously only been used in differential amplifiers for obtaining high DC gain, high output impedance and fast settling response (Wen-Whe, et al., 1998 and U.S. Pat. No. 6,762,646 B1). Here we design the folded-cascode topology, for buffering two current drivers namely the VCCS and the bidirectional current mirror circuits, each operating at different supply voltages, which was hitherto unknown in the prior art. Moreover, we identify breakdown voltage requirements for the transistors used to implement the folded cascode topology, specifically for NMES applications, which was previously unknown. We also disclose a method to simultaneously stimulate muscles using multiple output drivers interconnected to each other by the unity-gain buffers, which to the best of our knowledge was hitherto unknown.

In the following sections, several embodiments of the multistage driver circuit based NMES device are presented. While these embodiments discuss muscular stimulation per se, a person skilled in the art, can apply these embodiments for nerve stimulation also.

DETAILED DESCRIPTION—FIGS. 1-4—FIRST EMBODIMENT

Figure 1:
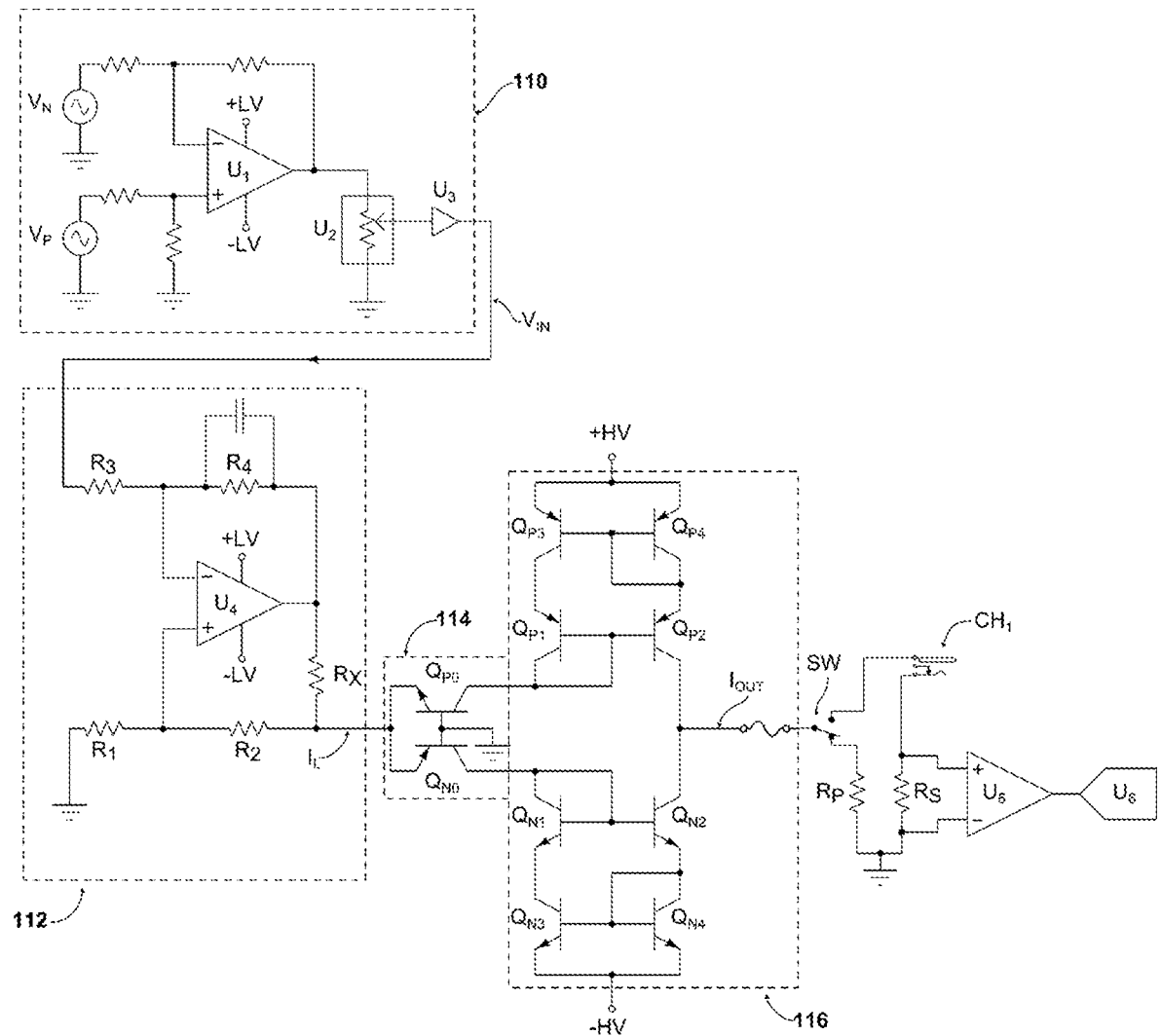
FIG. 1 is the schematic circuit diagram of a single channel of the neuromuscular electrical stimulator (NMES) with multistage driver circuit

In one embodiment shown in FIG. 1, the neuromuscular stimulator consists of a waveform generator 110, a voltage controlled current source (VCCS) 112, and output driving circuitry 114 and 116. The waveform generator 110 consists of a pair of signal generators $V_P$ and $V_N$ that connect to an operational amplifier (op-amp) $U_1$. The periods of $V_P$ and $V_N$ correspond to periods of the positive and negative phases of a biphasic stimulation waveform, respectively. In some embodiments, the periods and shape of $V_P$ and $V_N$ are generated by a microcontroller or by a digital-to-analog converter.

Op-amp $U_1$ is configured as a difference amplifier with adjustable gain, to compute the difference between $V_P$ and $V_N$. The amplitude of $V_P$ can also be scaled using the resistor divider network at the positive terminal of $U_1$, such that $V_P$ is a fraction of $V_N$. When $V_P$ is a fraction of $V_N$, the period of $V_P$ is proportionally increased by the microcontroller, such that net charge per phase (amplitude×period) is equal for both positive and negative phases of the biphasic stimulation waveform. Thus, by adjusting the amplitude and periods of the positive and negative phases, either symmetrical or asymmetrical waveforms can be generated. In some embodiments, the output of $U_1$ is scaled using a potentiometer $U_2$ to generate a graded input voltage $V_{IN}$, which is further buffered using a unity gain amplifier $U_3$.

$V_{IN}$ is connected to circuit 112, which is a VCCS known in the literature as the Howland current pump. The circuit of 112 consists of a low-voltage rated op-amp $U_4$ operating at ±LV (e.g. ±15V) and precision resistors $R_1$-$R_4$ and $R_X$. In some embodiments, a low-voltage, high-output current operational amplifier (e.g. LM7321, LM7372 from Texas Instruments) can be used in place of $U_4$. Further, it can be shown that when resistors in the positive and negative feedback paths of the op-amp in circuit 112 are selected such that $$\frac{R_1}{R_2 + R_X} = \frac{R_3}{R_4}, \quad (1)$$

then the load current $I_L$ is proportional to $V_{IN}$. Further, if $R_3=R_4$, then $$I_L = -\frac{V_{IN}}{R_X}. \quad (2)$$

Therefore by adjusting $V_{IN}$ or $R_X$, we can set the desired load current $I_L$ generated by 112. However, the compliance voltage of the VCCS is limited by its supply voltage to within ±LV.

To improve the output voltage compliance of the VCCS, the current $I_L$ is drives an output stage using a pair of folded cascode bipolar transistors ($Q_{N0}$, $Q_{P0}$) shown in 114. The common-base, folded cascode transistors 114 provide unity gain buffering between the VCCS 112 and a high-voltage bidirectional current mirror circuit 116. The bidirectional current mirror circuit is implemented using the modified Wilson's current mirror topology in 116. The circuit in 116 is symmetrical about the middle, with top half capable of sourcing current and bottom half capable of sinking current, and is powered by stepped-up DC-DC high voltage (±HV, e.g. ±150V). The current mirror topology can provide high output compliance=±HV, using low-cost, high-voltage rated transistors. If we select the PNP and NPN transistors (i.e., $Q_{P1}$-$Q_{P4}$ and $Q_{N1}$-$Q_{N4}$) to have identical DC current gains, then we can show that $$I_{OUT} = -I_L = \frac{V_{IN}}{R_X}. \quad (3)$$

Thus, in this embodiment, by buffering of the Howland current pump 112 and Wilson's current mirror circuits 116, using folded cascode topology 114, we create an adjustable, high-voltage compliant, constant current source. Note that it will be obvious to a person having ordinary skills in the art that the circuits shown in 112, 114, and 116 can be realized using either bipolar junction transistor or field effect transistor technology. Further, the above configuration can be implemented using either discrete components or fabricated as a monolithic integrated circuit (IC). Still further, while this embodiment presents specific examples of current source and current mirror circuits, the above embodiment can also be realized using alternative configurations, by a person skilled in the art.

In 116, when the folded-cascode and output transistors $QP_0$, $QP_2$ and $QN_0$, $QN_2$ are subjected to large reverse voltages, when they are in cutoff mode and the complementary current mirror circuit is active. Hence, these current transistors must be selected with collector-emitter breakdown voltage ($V_{CEO}$) greater than ±HV power supply, i.e. $V_{CEO} \geq 2*|HV|$. For example, transistors FZT758 and FZT658 from Diodes Inc., have $V_{CEO}>|400V|$, which is typically in the range for neuromuscular stimulation. The remaining current mirror transistors, namely $QP_1$, $QP_3$, $Q_{P4}$, $Q_{N1}$, $Q_{N3}$, and $Q_{N4}$ can be implemented with smaller $V_{CEO}$ requirement, however it is recommended to use same transistors as $Q_{P2}$ and $Q_{N2}$, for matching the DC current gains.

In the quiescent mode when no stimulation is being generated, the output driver is in cutoff and the maximum power dissipation occurs in the VCCS. In this conventional Howland pump using a high-voltage rated opamp (e.g. PA341DF from Cirrus Logic) with quiescent current 2.5 mA and supply voltage ±150V, the quiescent power dissipation is 750 mW. While in the present embodiment using a low-voltage rate opamp with similar output current capacity (e.g. LM7321 from Texas Instruments), having quiescent current 1.1 mA and ±15V supply, the quiescent power dissipation is 33 mW. Thus the present VCCS implementation is 95% more efficient than conventional Howland pump based designs.

To ensure safe operation of this embodiment during neuromuscular stimulation, the output current $I_{OUT}$ can be limited through a fuse before being delivered through $CH_1$, as shown in FIG. 1. Additionally, in an emergency situation, switch SW can immediately divert the current away from $CH_1$ by shunting the channel with low impedance load $R_P$. During normal operation, current $I_{OUT}$ can be measured in its return path using a series resistor $R_S$, a current sense amplifier $U_5$, and an analog-to-digital converter $U_6$. Further, in some embodiments, the current measured can be used as a feedback signal to adjust the load current $I_L$ and maintain desired output current $I_{OUT}$.

Figure 2:
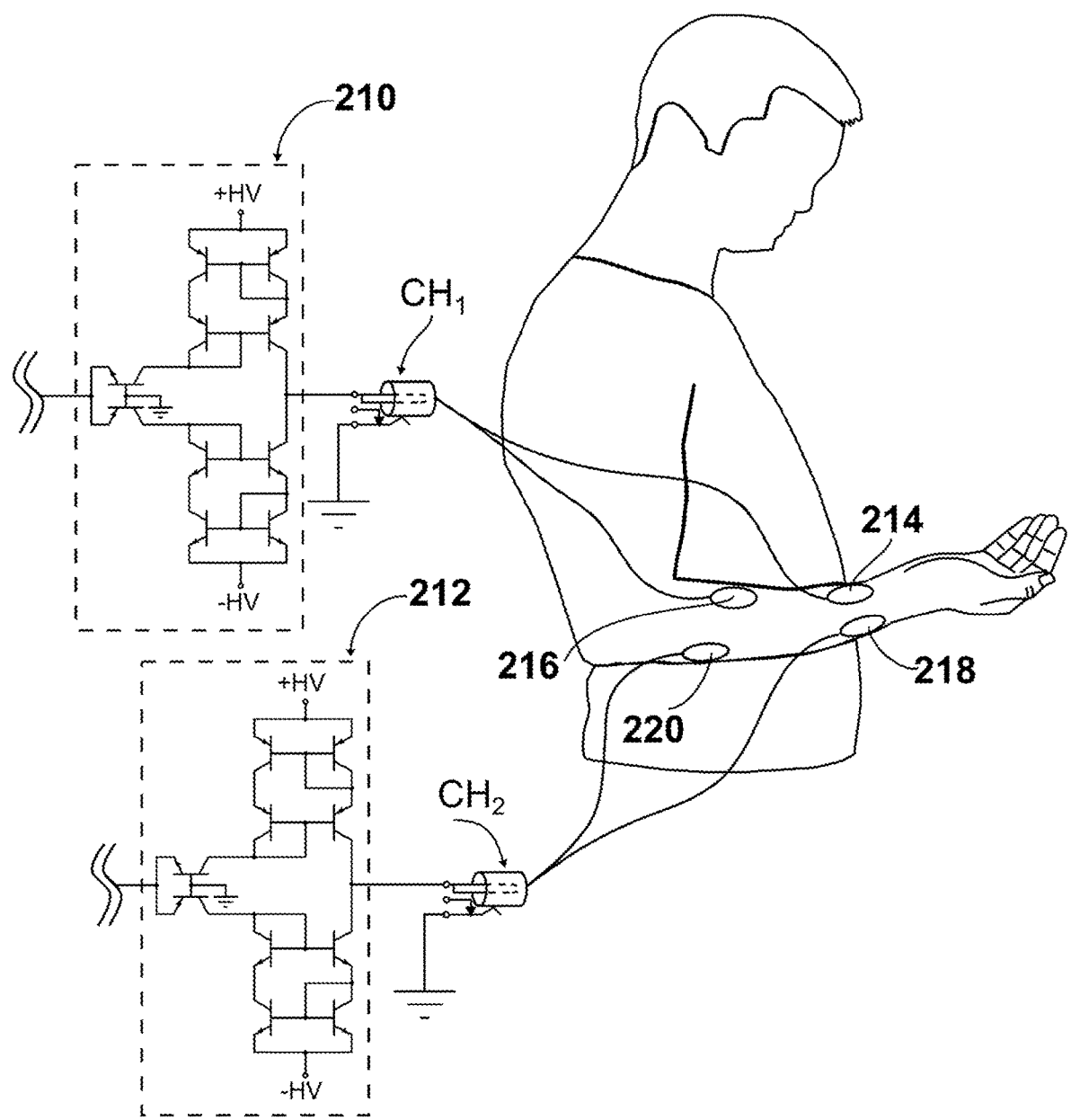
FIG. 2 illustrates one embodiment of the disclosed NMES for stimulating antagonist forelimb muscle pair of a patient

FIG. 2 illustrates one instance of the embodiment of FIG. 1 to electrically stimulate the forearm muscles of a patient. In FIG. 2, many aspects of $CH_1$ (FIG. 1) are hidden and some aspect of its output driving stage is reproduced in 210 for illustration purposes. A second stimulation channel $CH_2$ and its corresponding output driving stage 212, is illustrated for stimulating a second muscle segment. Lead wires of $CH_1$ and $CH_2$ are respectively connected to an antagonistic muscle pair, namely flexor digitorum and extensor digitorum muscles, using a pair surface electrodes (e.g. Model 650 from Covidien Inc.). In one embodiment, the current enters the muscles through one of the surface electrodes 216 or 220 placed over the muscle's belly and returns through either or both of the distally placed surface electrodes 214 and 218. In another embodiment, the entry and return paths of the currents are interchanged depending on the polarity of the current waveform.

Figure 3A:
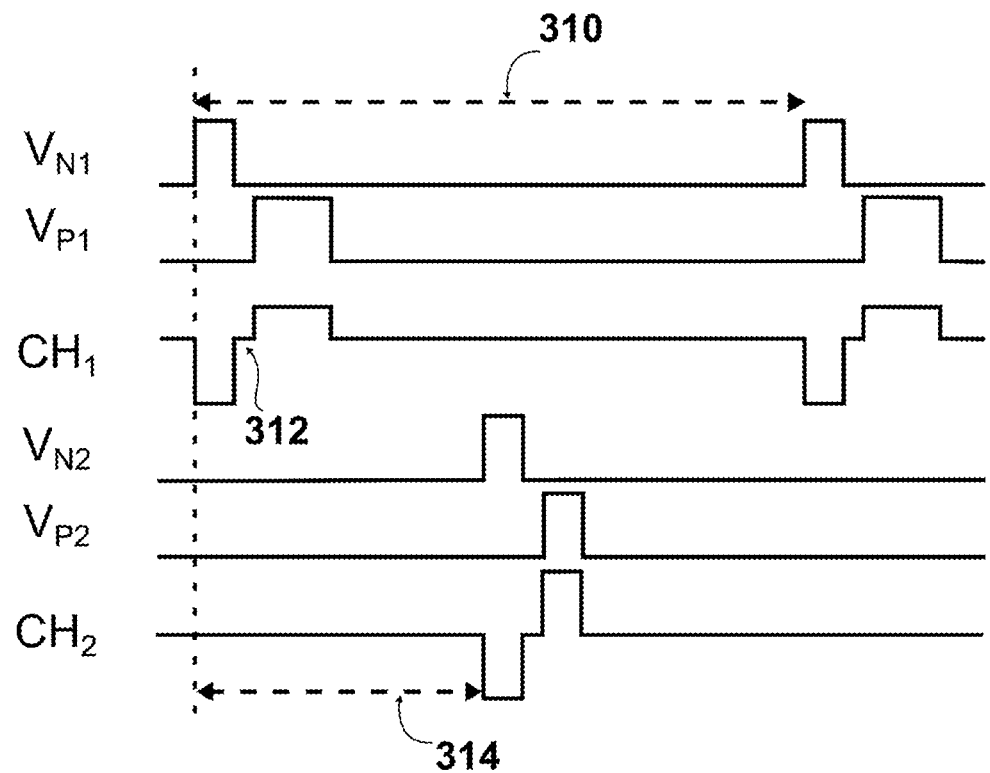
FIG. 3A shows an example of the timing profiles for the sequential activation of two stimulation channels of the NMES device.

In FIG. 3A, the timing profiles for stimulation channels $CH_1$ & $CH_2$ are shown. In the example illustrated in FIG. 3A, the periods and amplitudes of positive and negative phases are configured such that the waveforms of $CH_1$ and $CH_2$ are asymmetrical and symmetrical, respectively. In the prior art, it is known that the strength of muscle contractions are proportional to the amplitude and duration of the stimulation currents. Therefore, by adjusting the amplitude and duration of the waveforms of $CH_1$ and $CH_2$, we can control the response of individual muscles. Further, the stimulation repetition rate or frequency 310 (FIG. 3A) can be configured by the microcontroller to ensure sustained muscle contractions. In some embodiments, the negative and positive phases can be separated by an inter-pulse interval 312 to delay the onset of muscle fatigue. In the version shown in FIG. 3A, $CH_1$ and $CH_2$ occur sequentially separated by an inter-channel delay 314, such that the ensuing muscle contractions do not overlap. In other versions, the trains of pulses can be programmed to generate sustained contraction in one antagonistic muscle after another, allowing the patient for example, to completely open and then close their hand. In yet other versions, the antagonistic muscles can contract simultaneously and with different strengths, to produce a sustained but damped contraction in one direction.

Figure 3B:
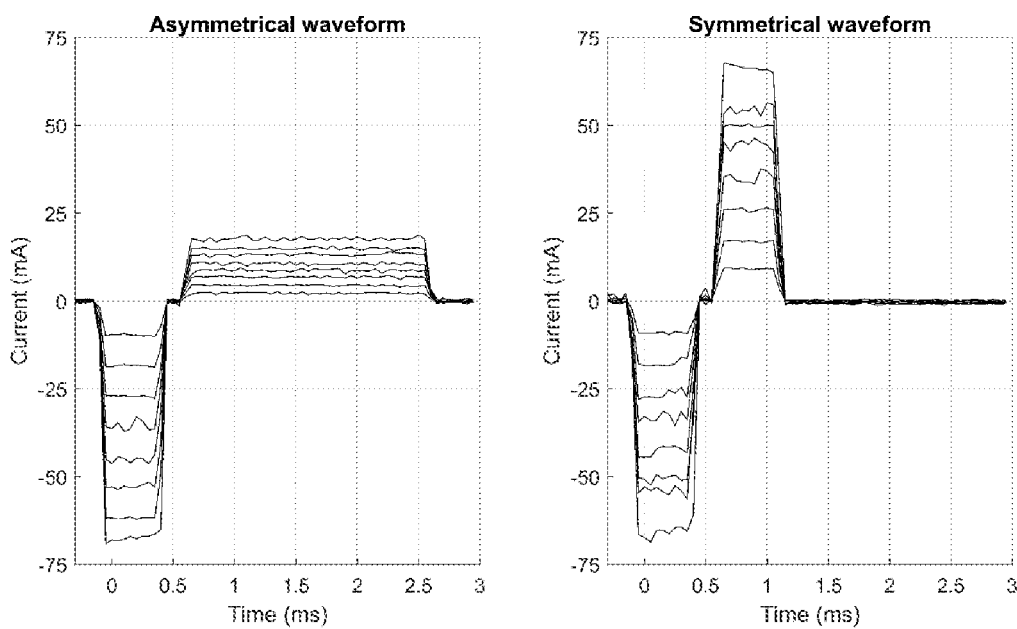
FIG. 3B illustrates sample current waveforms generated by the NMES device when configured for symmetrical and asymmetrical output

In FIG. 3B, sample waveforms recorded from the disclosed NMES system in FIG. 1 are shown. The left and right plots of FIG. 3B correspond to asymmetrical and symmetrical current waveforms, generated for different amplitudes ranging from 10 mA-70 mA, for a load impedance of 2 kilo-ohms (k$\Omega$). The negative phase duration was set at 500 micro-seconds ($\mu$s), and for the asymmetrical waveforms the positive pulse duration and amplitude were adjusted to maintain equal charge per phase. In this example, circuits 110 and 112 (FIG. 1) were powered with $\pm LV=\pm 15V$, whereas the output-driving stage 116 was powered with $\pm HV=\pm 150V$. To generate the low and high voltage supplies, step-down and step-up DC-DC converters were used respectively, which were operated by two 24V batteries. In the literature several topologies of DC-DC converters are known and a person skilled in the art can implement it using alternative topologies, requiring even lower voltage batteries.

Figures 4A, 4B:
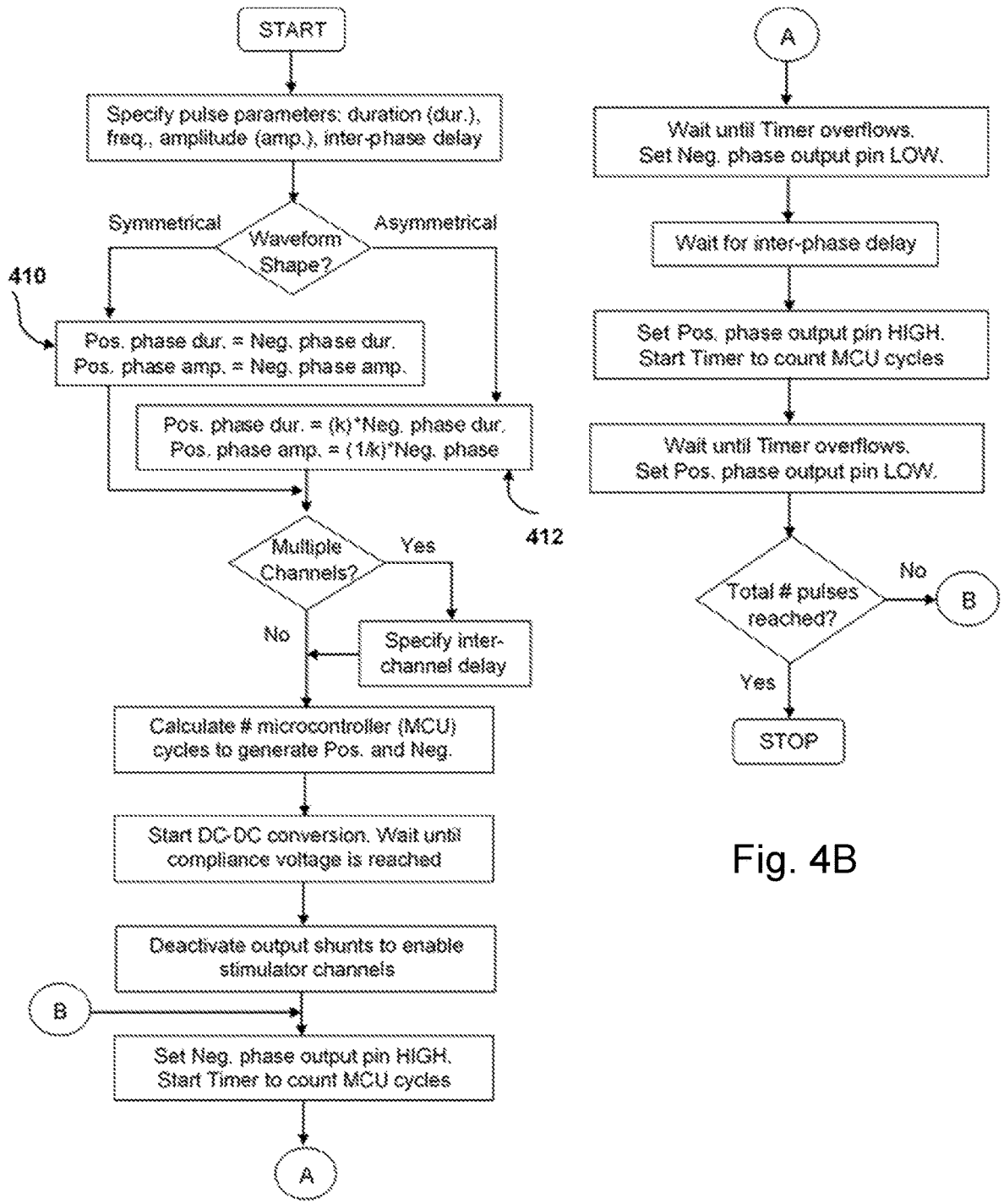
FIGS. 4A and 4B are flowcharts that diagrammatically illustrate the microcontroller's program for operating the NMES device

The microcontroller's normal sequence of execution is briefly described in the flowcharts of FIGS. 4A and 4B. At the start, the user uses a graphical user interface (GUI) to specify the stimulation parameters such as pulse-duration, amplitude, inter-phase delay, etc. Depending on the desired waveform shape, either symmetrical 410 or asymmetrical 412 phase durations and amplitude are configured. In 412, the phase and amplitude of positive and negative phases can be scaled by parameter (k), in order to maintain equal charge balance for each phase. For a given pulse duration, the microcontroller computes the number of cycles for which the voltage on each waveform generator signal must remain HIGH. A digital Timer keeps track of the number of microcontroller cycles executed and after the desired interval, the voltage is returned to LOW. The sequence of operations are repeated in a loop, until the desired the number of stimulation pulses have been generated. Prior to activating the stimulator, the step-up DC-DC converter is turned on and a few milliseconds (ms) delay is introduced, so as to reach the desired compliance voltage. Any time during the program execution, if the emergency OFF switch is pressed by the patient or a fault occurs, the program interrupts the microcontroller and shunts all stimulation channels using low impedance loads.

DETAILED DESCRIPTION—FIGS. 5-7—OTHER EMBODIMENTS

Figure 5:
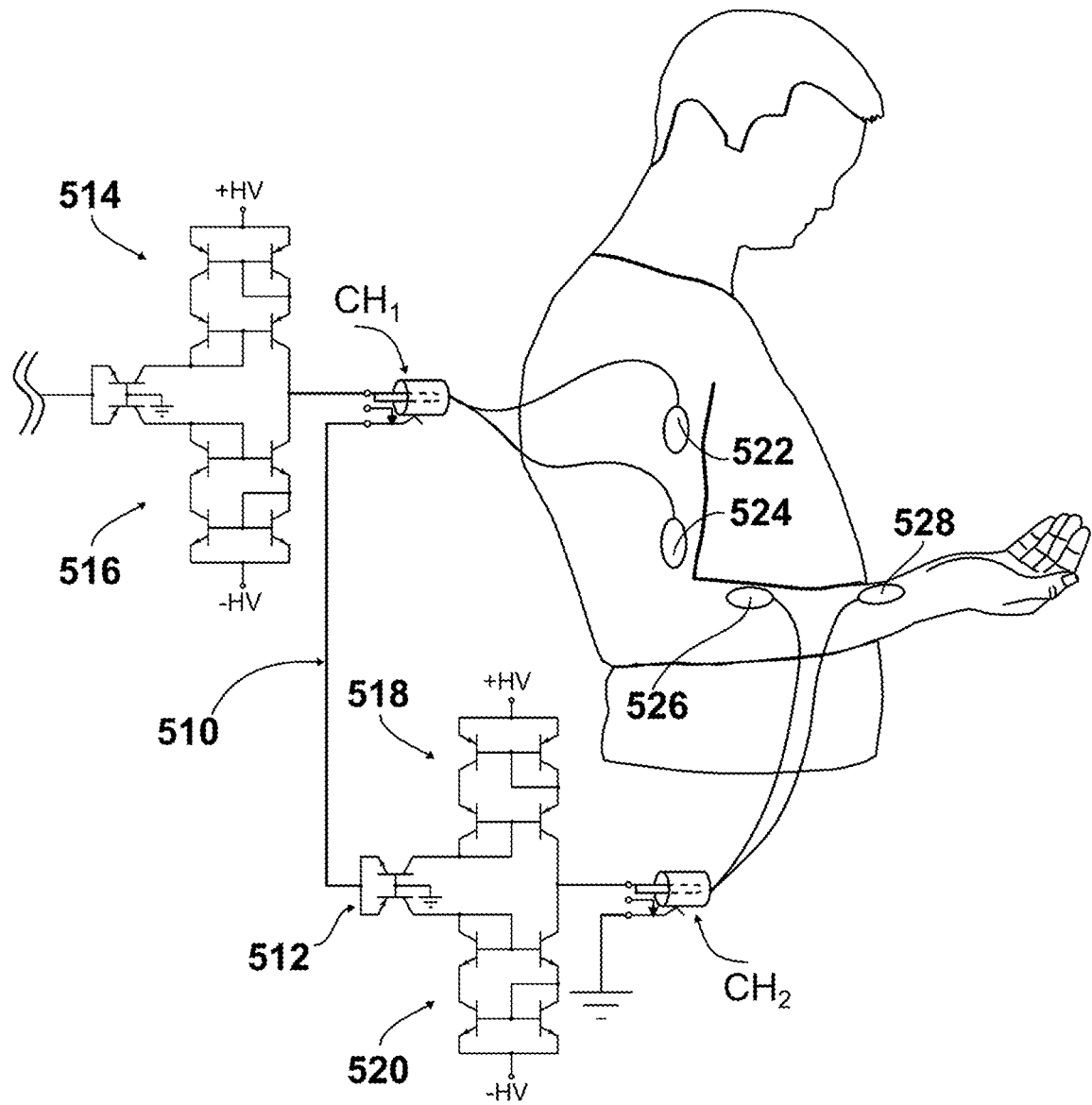
FIG. 5 presents another embodiment of the disclosed NMES for simultaneously stimulating multiple muscles using a single VCCS FIG. 6 extends the embodiment from FIG. 5 and illustrates simultaneous stimulation of several muscles using a single VCCS

FIG. 5 illustrates a second embodiment of the disclosed NMES device. In this setup, the return path of channel $CH_1$ via conductor 510 is connected to the folded cascode buffer stage 512 of channel $CH_2$ and the return path of $CH_2$ completes the circuit. When the PNP transistor-based current mirror circuit 514 of $CH_1$ sources current, it causes the NPN transistor-based current mirror to simultaneously sink current through $CH_2$. Likewise, when the complementary circuit 516 sinks current through $CH_1$, it causes circuit 518 to source current to $CH_2$. Alternately, when current is applied at electrode sites 522 and 524 by $CH_1$, an equal and inverted current is simultaneously applied at electrode sites 526 and 528 by $CH_2$. This will cause the muscles connected to $CH_1$ and $CH_2$ to simultaneously contract. Thus, in this embodiment using a single voltage-controlled current source (VCCS) we can simultaneously deliver equal amounts of current to both muscles. This is depicted in the illustrative example shown FIG. 5, where the biceps and flexor digitorum muscles can be simultaneously contracted using a single VCCS. This movement is useful during simultaneous reaching and grasping tasks, e. g. eating with a spoon.

While it is possible to directly connect multiple muscles using series or parallel combinations and stimulate them with a single stimulator, this approach has significant limitations. Firstly, in the case when the muscles are connected in series, the tissue impedance of each muscle will add up and the effective tissue impedance will increase. In this case, to maintain voltage compliance in the presence of large effective impedance, a higher power supply will be required which will increase the device cost. Secondly, for the case when multiple muscles are connected in parallel, the current through each individual muscles will be reduced according to Kirchhoff's current law, which will reduce the overall stimulation efficacy. Thus, our multistage current driver circuit is beneficial over conventional series or parallel topologies for simultaneously stimulating multiple muscle groups.

Figure 6:
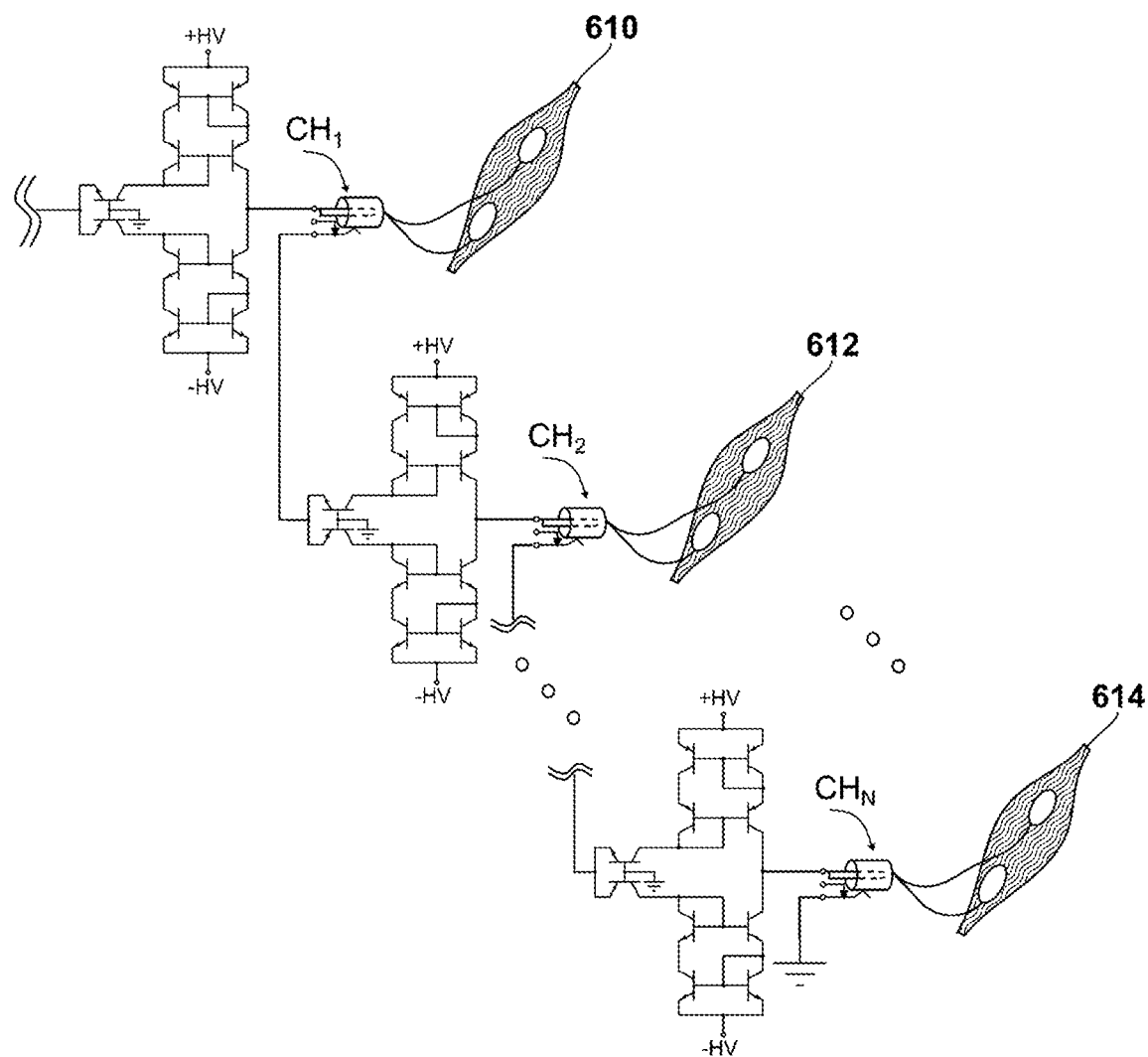

In FIG. 6, the embodiment from FIG. 5 is extended to 'N' muscles such that the return path of previous output stage drives current into the next output stage. Thus, using a plurality of output drivers connected in series, a single VCCS can drive equal currents through channels $CH_1$, $CH_2$, up to $CH_N$ and simultaneously activate multiple muscles, as represented in FIG. 6 by 610, 612, and 614, respectively. This embodiment can be employed for movements that require simultaneous activation of muscles synergies, for e.g. in sit to stand training, in bilateral upper-limb training for holding a glass in one hand and pouring water with another, and in gait training for simultaneous activation lower-limb muscles during the stance and swing phases.

Figure 7:
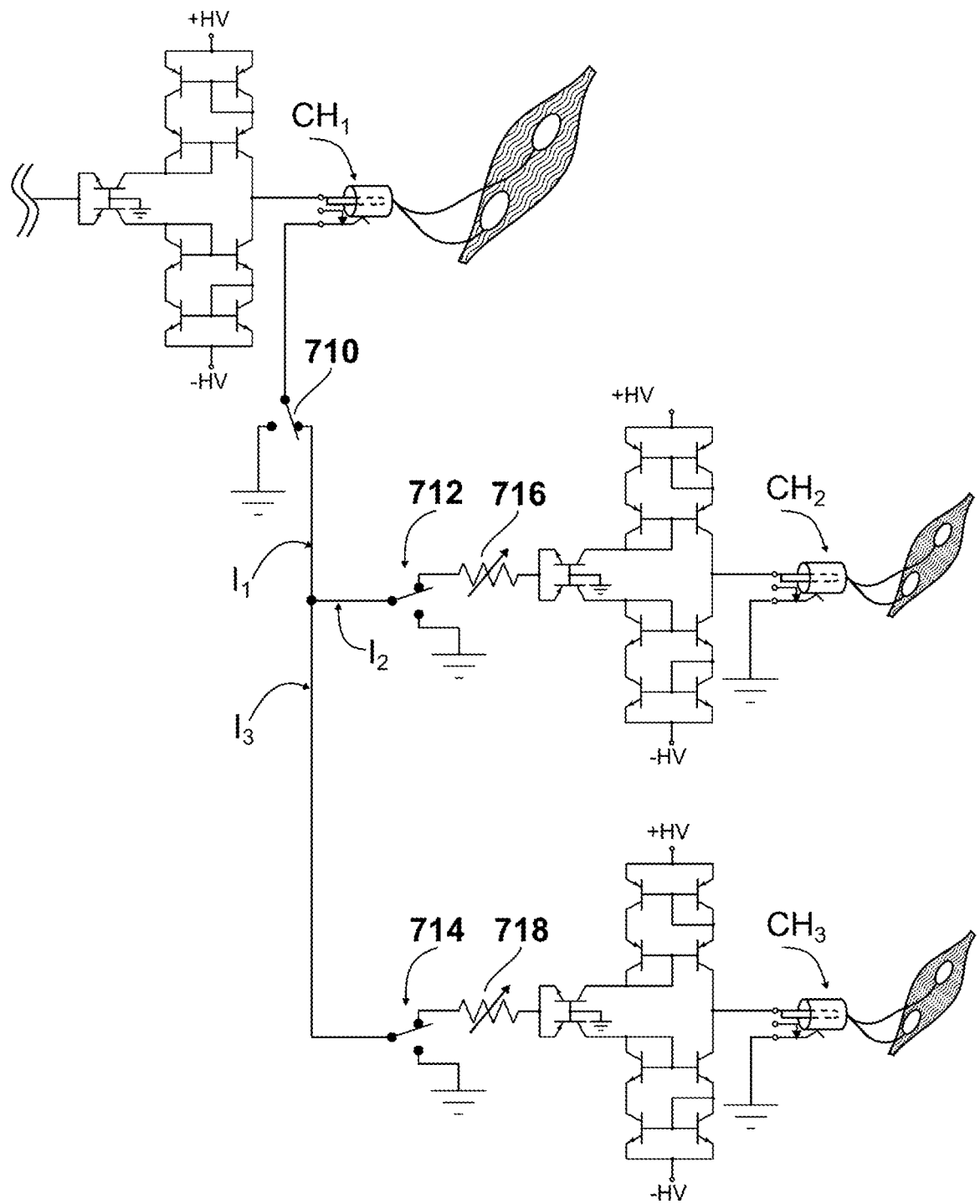
FIG. 7 illustrates the multistage NMES device for simultaneously and selectively stimulating large as well as small muscles.

In another embodiment illustrated in FIG. 7, a network of switches 710, 712, and 714 are used to selectively connect $CH_1$ with both, either or none of the subsequent output drivers controlling stimulation channels $CH_2$ and $CH_3$. This provides the NMES device the capability to selectively activate or deactivate certain muscles pairs. When both channels $CH_2$ and $CH_3$ are connected in the return path of CH1, variable resistors 716 and 718 can be used to proportionally divide the current $I_1$, such that $I_1=I_2+I_3$. This embodiment will allow for simultaneous stimulation of a large muscle that requires higher current intensity and multiple smaller muscles that require lower current intensities, e.g. stimulating the forearm and hand muscles during grasping.

What is claimed is:

1. A neuromuscular electrical stimulator, comprising:
   a waveform generator having a symmetrical and symmetrical output;
   a bidirectional voltage controlled current source having an output voltage less than 100 volts;
   a bidirectional current mirror circuit connected to an output of the bidirectional voltage controlled current source,
      wherein a current output by the bidirectional current mirror circuit has a same value and a higher voltage as a current output by the bidirectional voltage controlled current source;
   a unity gain current buffer connected to the output of the bidirectional voltage controlled current source and an input to the bidirectional current mirror circuit; and
   a biological interface, wherein the biological interface includes at least a working electrode and a return electrode to deliver the current output by the bidirectional current mirror circuit.

2. The stimulator of claim 1, wherein the bidirectional voltage controlled current source lacks an op-amp rated at 100 volts or higher.

3. The stimulator of claim 1, wherein
the stimulator includes a single and only bidirectional voltage controlled current source,
the single and only bidirectional voltage controlled current source is a bidirectional Howland current pump,
the current mirror circuit is a bidirectional current mirror circuit with a sourcing current portion and a sinking current portion, and
both the sourcing current portion and the sinking current portion receive the output of the single and only bidirectional voltage controlled current source.

4. The stimulator of claim 1, wherein the bidirectional voltage controlled current source, the bidirectional current mirror circuit, and the unity gain current buffer comprise a multistage driver and wherein the waveform generator includes a plurality of independent channels, the stimulator further comprising:
a plurality of the multistage drivers each coupled to one channel of the plurality of independent channels.

5. The stimulator of claim 1, wherein the bidirectional current mirror circuit, and the unity gain current buffer comprise an output driver, the stimulator further comprising:
a single and only bidirectional voltage controlled current source; and
a plurality of the output drivers each coupled in series or parallel with one another,
wherein the single and only bidirectional voltage controlled current source is connected to the output drivers.

6. The stimulator of claim 5, further comprising:
a network of switches and resistors to selectively attenuate or divert the electrical signals supplied by the plurality of output drivers.

7. The stimulator of claim 1, further comprising:
a controller including a processor and memory, wherein the controller is configured to instruct the waveform generator to output digital waveform electrical pulses and turn on step-up DC-DC converters connected to the stimulator to provide a desired operating voltage to the stimulator prior to operating the stimulator.

8. The stimulator of claim 7, wherein the controller is configured to receive stimulation parameters input from a graphical user interface on a connected computer.

9. The stimulator of claim 7, wherein the controller includes a plurality of interrupts configured to deactivate the stimulator upon activation of an emergency off switch.

10. The stimulator of claim 7, wherein the biological interface is a skin interface including a plurality of electrodes configured to attach to human skin and deliver the current to at least one nerve or muscle beneath the skin.

11. The stimulator of claim 1, wherein the bidirectional current mirror circuit, and the unity gain current buffer comprise an output driver, the stimulator further comprising:
a first output driver and a second output driver, each output driver connected to a corresponding biological interface, wherein
the second output driver receives an input from the return electrode of the biological interface connected to the first output driver.

12. A multistage driver for a neuromuscular electrical stimulator, the driver comprising:
a bidirectional voltage controlled current source means;
a unity gain current buffer means connected to an output of the bidirectional voltage controlled current source means; and
a bidirectional current mirror circuit means connected to an output of the unit gain current buffer means.

13. The multistage driver of claim 12, wherein the multistage driver lacks an op-amp rated at 100 volts or higher.

14. The multistage driver of claim 12, wherein the bidirectional current mirror circuit means, and the unity gain current buffer means comprise an output driver, the multistage driver further comprising:
a plurality of the output drivers each coupled in series or parallel with one another, and wherein a network of switches and resistors are configured to selectively attenuate or divert the electrical signals supplied by the plurality of output drivers.

15. The multistage driver of claim 12, wherein the voltage controlled current source means is configured to produce a symmetrical and symmetrical biphasic electrical waveform at any voltage, and
wherein the controlled current source means is configured to reproduce the biphasic electrical waveform at a threshold voltage for nerve or muscle stimulation.

16. A method of electrically stimulating nerves or muscles, the method comprising:
receiving, at a bidirectional voltage controlled current source from a waveform generator, an electrical signal, wherein the bidirectional voltage controlled current source has an output voltage less than 100 volts, the bidirectional voltage controlled current source is connected to a bidirectional current mirror circuit through a unity gain current buffer; and
outputting, from the bidirectional current mirror circuit, the electrical signal to a biological interface including at least a working electrode and a return electrode.

17. The method of claim 16, wherein the bidirectional voltage controlled current source is a bidirectional Howland current pump and is the single and only bidirectional voltage controlled current source that outputs voltage less than 100 volts,
wherein the bidirectional current mirror circuit is a bidirectional current mirror circuit with a sourcing current portion and a sinking current portion, and
both the sourcing current portion and the sinking current portion receive the output of the single and only bidirectional voltage controlled current source.

18. The method of claim 16, further comprising:
attaching the biological interface to an external human skin position over a nerve or muscle to be stimulated.

19. The method of claim 18, the bidirectional voltage controlled current source is the single and only bidirectional voltage controlled current source that outputs voltage less than 100 volts, and additional nerves or muscles are simultaneously stimulated, and wherein the method further comprising:
receiving, at a plurality of output drivers from the single and only bidirectional voltage controlled current source, the electrical signal, wherein each output driver include the bidirectional current mirror circuit, and the unity gain current buffer,
outputting, from the plurality of output drivers, the simultaneous electrical signal to the additional nerves or muscles.

20. The method of claim 16, wherein the waveform generator is controlled by a controller including a processor and memory that instructs the waveform generator to output digital waveform electrical pulses and turn on step-up DC- DC converters connected to the stimulator to provide a desired operating voltage to the stimulator prior to operating the stimulator, wherein the waveform is biphasic and one of symmetrical and asymmetrical output.

\* \* \* \* \*